United States Patent [19]
Crivello et al.

[11] Patent Number: 6,124,418
[45] Date of Patent: Sep. 26, 2000

[54] SELECTIVE CATALYSTS FOR THE SYNTHESIS OF EPOXYSILICONE MONOMERS AND POLYMERS

[75] Inventors: James Vincent Crivello, Clifton Park; Mingxin Fan, Troy, both of N.Y.

[73] Assignee: General Electric Company, Pittsfield, Mass.

[21] Appl. No.: 08/195,897

[22] Filed: Feb. 14, 1994

Related U.S. Application Data

[63] Continuation of application No. 07/896,935, Jun. 11, 1992, abandoned.
[51] Int. Cl.$^7$ .............................. C08G 77/06; C08G 77/08
[52] U.S. Cl. .............................. 528/15; 528/23; 528/419; 528/421
[58] Field of Search .................................. 528/27, 15, 23, 528/419, 421; 549/215

[56] References Cited

U.S. PATENT DOCUMENTS

| | | | |
|---|---|---|---|
| 4,083,856 | 4/1978 | Mendicino | 528/27 |
| 4,617,238 | 10/1986 | Crivello et al. | 428/452 |

FOREIGN PATENT DOCUMENTS 0 288 286  10/1988  European Pat. Off. .

OTHER PUBLICATIONS

International Polymer Science and Technology vol. 16, No. 7, 1989.
Chemical Abstract, vol. 110 8268D (1989).
Chemical Abstract, vol. 109 149782h Journal of Polymer Sci, Vo. 28, P484–486.
Iovel, I G. et al., "Quaternary Onium Hexachloroplatinats,: Novel Hydrositylation Catalyst", Organometallics, vol. 6, pp. 1410–1413 (1987).
J.L. Speier, Advances in Organometallic Chemistry, vol. 17, pp 407–447, FGA Stone and R West, eds., Academic Press (1979).
Crivello and Lee, Journal of Polymer Science, vol. 28, pp 479–503, John Wiley & Sons (1990).
Schweizer and Kerr, "Thermal Decomposition of Hexachloro Platinic Acid" in Inorganic Chemistry, vol. 17, pp. 2326–2327, (1978).
Lewis, Journal of the American Chemical Society, vol. 112, p 5998 (1990).
"Novel Platinum Containing Initiators for Ring–Opening Polymerizations", Polymer Science, Pt. A, Polymer Chem. Edition, vol. 29, pp 1853–1863 (1991).

*Primary Examiner*—Robert Dawson
*Attorney, Agent, or Firm*—Kenneth S. Wheelock

[57] ABSTRACT

The invention provides a method for making a curable epoxysilicone composition through the hydrosilation reaction between an ethylenically unsaturated epoxide and an SiH-containing silicone to produce an epoxysilicone product, and catalyzed by a quaternary ammonium, phosphonium or arsonium hexahaloplatinate which does not promote the oxirane ring-opening reaction of either the ethylenically unsaturated epoxide starting material or the epoxysilicone product. The invention also provides for a curable epoxysilicone composition made by the above method.

7 Claims, No Drawings

SELECTIVE CATALYSTS FOR THE SYNTHESIS OF EPOXYSILICONE MONOMERS AND POLYMERS

This is a continuation of of application Ser. No. 07/896,935 filed on Jun. 11, 1992 and now abandoned.

The invention relates to a method of producing epoxysilicones via catalysts which promote a hydrosilation addition reaction between an ethylenically unsaturated epoxide and an organohydrogensilane or organohydrogensiloxane, without also promoting the oxirane ring-opening polymerization of the ethylenically unsaturated epoxide starting material or the epoxysilicone hydrosilation reaction product. The invention also relates to a curable epoxysilicone composition made by the present method.

BACKGROUND OF THE INVENTION

In the production of epoxysilicone compositions, transition metal catalysts have long been known to promote the hydrosilation reaction. See, for example, J. L. Speier, "Homogeneous Catalysis of Hydrosilation by Transition Metals", in *Advances in Organometallic Chemistry*, Vol. 17, pp. 407–447, F. G. A. Stone and R. West, eds., Academic Press (New York, San Francisco, London), 1979; Aylett, *Organometallic Compounds*, Vol.1, p. 107, John Wiley & Sons (New York), 1979; and Crivello and Lee, "The Synthesis, Characterization, and Photoinitiated Cationic Polymerization of Silicon-Containing Epoxy Resins", *J. Polymer Sci.*, Vol. 28, pp. 479–503, John Wiley & Sons (New York), 1990. Generally, the hydrosilation catalysts used are complexes of platinum, palladium, rhodium, iridium, iron or cobalt. In particular, platinum-containing catalysts have been widely used for this purpose.

The most commonly used platinum-containing hydrosilation catalysts are those derived from chloroplatinic acid. These catalysts tend to be unstable and to form metal cluster compounds or colloids (Cotton and Wilkenson, in *Advanced Inorganic Chemistry*, 4th edit., John Wiley and Sons (New York), 1980). Chloroplatinic acid itself is both thermally and photochemically unstable in solution. In addition, its composition is variable depending on its state of hydration. For example, chloroplatinic acid typically contains the $H_3O^+$, $H_5O_2^+$, and $H_7O_3^+$ ions. On standing in solution at room temperature, chloroplatinic acid will oftentimes deposit elemental platinum. On thermal decomposition, volatile $Pt_6Cl_{12}$ is also formed as one of the intermediates (Schweizer and Kerr, "Thermal Decomposition of Hexachloroplatinic Acid" in *Inorganic Chemistry*, vol. 17, pp. 2326–2327, 1978).

It has been found that in addition to catalyzing the hydrosilation reaction, many transition-metal-complex catalysts in the presence of silicon hydrides also promote the oxirane ring-opening polymerization of the ethylenically unsaturated epoxide starting material and the epoxysilicone product of the hydrosilation reaction. Reference is made, for example, to copending, commonly assigned application Ser. No. 07/473,802 (Riding, et al.), filed Feb. 2, 1990, now U.S. Pat. No. 5,128,431 which discloses the use of platinum or platinum-based catalysts to promote the oxirane ring-opening polymerization of epoxides. This ring-opening polymerization reaction during production of an epoxysilicone is undesirable as the epoxide polymerization may cause the reaction mixture to gel completely, resulting in the loss of the entire batch and in loss of considerable time in cleanup of the insoluble gelled resin.

Additionally, a partial gelation due to the ring-opening polymerization reaction can occur during epoxysilicone synthesis such that reproducible batch-to-batch viscosity of the epoxysilicone product is difficult to obtain. Such reproducibility in viscosity is highly preferred in the epoxysilicone industry, as these materials are typically used as coatings, for example release coatings, and the process of successfully and uniformly applying these coatings to a substrate is highly dependent upon the viscosity of the coating material. Commonly assigned, copending applications to Eckberg, et al., Ser. No. 07/802,679, now U.S. Pat. No. 5,227,410 and Ser. No. 07/802,681 U.S. Pat. No. 5,240,971, both filed Dec. 5, 1991, disclose that viscosity control can be achieved by use of a tertiary amine stabilizer during the hydrosilation synthesis reaction. However, only a limited number of transition-metal hydrosilation catalysts are active in the presence of this stabilizer.

In the presence of precious metal hydrosilation catalysts, epoxysilicones have been found to slowly gel on storage at room temperature due to the epoxide ring-opening polymerization reaction, thus shortening the shelf-life of the epoxysilicone product. While this storage problem can be partially alleviated by deactivating the transition-metal-complex catalyst with an inhibitor of its catalytic activity, such as dodecyl mercaptan or 2-mercaptobenzothiazole in the case of platinum complexes, it would be preferable to not incorporate this extra component and additional process step into epoxysilicone composition and production process.

In most of the catalytic systems involving platinum complexes, the catalytic species is not well understood. Recently, colloids have been shown to be the active species involved in some of catalytic hydrosilation reactions (Lewis, *Journal of the American Chemical Society*, vol. 112, p. 5998, 1990) and in the ring-opening polymerization of epoxides ("Novel Platinum Containing Initiators for Ring-Opening Polymizations", Journal of Polymer Science, Pt. A; Polymer Chemistry Edition, Vol. 25, 1853–1863, 1991.) Other reports suggest that the catalytic species in the hydrosilation reaction is a non-colloidal metal complex (See, for example, Harrod and Chalk, in *Organic Synthesis Via Metal Carbonyls*, p.673, Wender and Pino, eds., John Wiley & Sons (New York), 1977).

In order to minimize the oxirane ring-opening polymerization reaction, epoxysilicone fluids have been previously successfully produced only by careful control of batch temperature and olefin epoxide feed rate during the synthesis, followed by the above-mentioned inactivation of the catalyst after the completion of the hydrosilation reaction.

As disclosed in commonly assigned U.S. Pat. No. 5,169,962 of Crivello and Fan, entitled "Preparation of Epoxysilicon Compounds using Rhodium Catalysts", certain rhodium-based hydrosilation catalysts selectively promote the hydrosilation reaction without the promotion of an epoxide ring-opening polymerization reaction. A variety of epoxy-containing silicone monomers and oligomers can be synthesized using these catalysts. However, most of the catalysts traditionally used for synthesis of epoxysilicone compositions, particularly Pt-containing catalysts, promote the epoxide ring-opening polymerization reaction, and therefore do not permit the selective hydrosilation synthesis of epoxysilicones.

The use of certain quaternary onium hexachloroplatinates as catalyst for the hydrosilation reaction between phenylacetylene and triethylsilane has been previously described. Reference is made to Iovel, I., Goldberg, Y., Shymanska, M. and Lukevics, E., in *Organometallics*, vol. 6, pp. 1410–1413, 1987. However, this study did not indicate the suitability of the quaternary onium hexachloroplatinates as useful hydrosilation catalysts for addition to vinyl epoxides, nor did it suggest that such salts effectively suppress the catalyst-dependent ring-opening polymerization of epoxy groups in either the starting ethylenically unsaturated epoxide or the epoxysilicone product of the hydrosilation reaction.

In consideration of the above, it is apparent that there exists a need in the epoxysilicone industry for a method of eliminating the oxirane ring-opening when employing commonly used hydrosilation catalysts. There also exists a need for an efficient yet economical method of producing epoxysilicone monomers and oligomers in the absence of the epoxide ring-opening side reaction, thereby generating epoxysilicone compositions of reproducible batch-to-batch viscosity. There is additionally a need for epoxysilicone composition which is stable to the epoxide ring-opening reaction and, therefore, has an increased shelf-life without the additional step and cost of poisoning the catalyst after the completion of the hydrosilation addition reaction.

Thus, it is an object of the present invention to provide a method for preparing an epoxysilicone composition through the reaction between an ethylenically unsaturated epoxide and an organohydrogensilane or organohydrogensiloxane in the presence of a catalyst which efficiently promotes the hydrosilation reaction without also promoting the aforementioned oxirane ring-opening polymerization of either the ethylenically unsaturated epoxide starting material or the epoxysilicone product.

It is another object of the invention to provide a hydrosilation catalyst for the addition reaction between an olefin epoxide and a SiH-containing silane or siloxane to form an epoxysilicone compound, wherein the catalyst effectively promotes the hydrosilation reaction without also promoting the ring-opening polymerization of the epoxide ring in either the olefin epoxide starting material or the epoxysilicone product.

Still another object of the invention is to provide a curable epoxysilicone composition with reproducible batch-to-batch viscosity and enhanced storage life, and which is stable to oxirane ring-opening polymerization at room temperature.

SUMMARY OF THE INVENTION

The present invention provides a method for making an epoxy-containing organosilicone compound, comprising the steps of:
(i) preparing a mixture comprising:
(A) 1 part by weight of an ethylenically unsaturated epoxide;
(B) from about 0.5 to about 400 parts by weight of an organohydrogensiloxane or an organohydrogensilane, as compared to the weight of (A); and
(C) from about 1 to about 5000 parts per million by weight as compared to the weight of (A) a hydrosilation catalyst of the formula

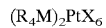

wherein M is arsenic, phosphorous or nitrogen, X is Cl⁻ or Br⁻, and R is an organic radical comprising $C_{1-30}$, substituted or unsubstituted, linear alkyl radical, or an aryl, alkaryl or aralkyl radical; and
(ii) reacting the mixture of said step (i), at a temperature of from about 25° C. to about 120° C. under conditions which promote a hydrosilation addition reaction between (A) and (B) to produce an epoxysilicone product, and which do not promote an epoxide ring-opening reaction in either (A) or in said epoxysilicone product.

The invention also provides a curable composition derived from Components (A), (B) and (C) and the method described above. The curable composition of the invention has the desirable qualities of batch-to-batch reproducibility in viscosity and enhanced storage life at room temperature.

DETAILED DESCRIPTION OF THE INVENTION

The present invention is based on the unexpected discovery that quaternary bis(onium) hexahaloplatinates are effective for promoting the addition of ethylenically unsaturated epoxides to silicon hydrides without also promoting the oxirane ring-opening polymerization reaction of the epoxide starting material or the epoxysilicone final product.

Although not intending the present invention to be limited by the mechanism of operation of the quaternary salt in increasing the specificity of a hexahaloplatinate catalyst for the hydrosilation reaction, it is believed that the onium salt stabilizes the active catalytic platinum species, and prevents the formation of colloidal platinum.

The present invention provides a method for making an epoxy-containing organosilicone compound, comprising the steps of:
(i) preparing a mixture comprising:
(A) 1 part by weight of an ethylenically unsaturated epoxide;
(B) from about 0.5 to about 400 parts by weight of an organohydrogensiloxane or an organohydrogensilane, as compared to the weight of (A); and
(C) from about 1 to about 5000 parts per million by weight as compared to the weight of (A) a hydrosilation catalyst of the formula

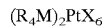

wherein M is arsenic, phosphorous or nitrogen, X is Cl⁻ or Br⁻ and R is an organic radical comprising $C_{1-30}$, substituted or unsubstituted, linear alkyl or, or an aryl, alkaryl or aralkyl radical; and
(ii) reacting the mixture of said step (i), at a temperature of from about 25° C. to about 120° C. under conditions which promote a hydrosilation addition reaction between an olefin epoxide and a silicon hydride to produce an epoxysilicone product, and which do not promote an epoxide ring-opening reaction in either the olefin epoxide or in the epoxysilicone product.

The invention also provides a curable composition derived from Components (A), (B) and (C) and the method of the invention described above.

By not promoting the oxirane ring-opening polymerization reaction, the method of the present invention allows the synthesis of highly reactive, curable epoxysilicones with improved viscosity control and without the danger of gelation during or after synthesis. Such curable epoxysilicones are useful in the production of, for example, silicone paper release agents, decorative and protective coatings, ink, adhesives, electronics encapsulants and insulation and other uses of epoxysiloxanes.

Component (A) used in the method and composition of the present invention is an ethylenically unsaturated, i.e., either vinyl- or allyl-functional, epoxide. The ethylenically unsaturated epoxides useful in Component (A) generally include any aliphatic (glycidyl) or cycloaliphatic epoxy compounds having olefinic moieties which will readily undergo the hydrosilation addition reaction to organohydrogensilicone compounds of Component (B). Commercially available examples of such ethylenically unsaturated epoxides useful in the practice of the invention include allyl glycidyl ether; methallyl glycidyl ether; 1-methyl-4-isopropenyl cyclohexene oxide; 2,6-dimethyl-2,3-epoxy-7-octene; 1,4-dimethyl-4-vinylcyclohexene oxide; 4-vinylcyclohexene oxide; vinylnorbornene monoxide; dicyclopentadiene monoxide. Other suitable examples of useful ethylenically unsaturated epoxides include 1,2-epoxy-6-heptene, 1,2-epoxy-3-butene and chemically similar, unsaturated aliphatic, cycloaliphatic, and alkylaromatic epoxides.

The preferred ethylenically unsaturated epoxide is 4-vinylcyclohexene oxide.

Component (B) is an organohydrogensiloxane or organohydrogensilane. Suitable silicon hydride-containing starting materials generally include any silicon compound derived from a silane or at least two organosiloxane units having terminal and/or pendant SiH groups. The SiH-containing silicones useful in the practice of the invention are those capable of reacting with the ethylenically unsaturated moieties of the epoxides of Component (A) above via the hydrosilation addition reaction.

Component (B) may be either a linear hydrogen substituted polysiloxane or silane or a cyclic hydrogen substituted polysiloxane or silane, or a combination of the two. The linear hydrogen substituted polysiloxane or silane may be either branched or unbranched. In addition, Component (B) organohydrogensiloxanes useful in the invention may be copolymers, terpolymers, etc. Illustrative Examples of such copolymers are a poly(dimethyl siloxane)-poly (methylhydrogen siloxane) copolymer or, when UV cure in conjunction with onium salt catalysts is desired in the curable composition of the present invention, a polyether/hydrogensiloxane linear block copolymer, such as described in copending, commonly assigned U.S. Patent application of Eckberg, et al., Attorney Docket 60SI-1466, filed Dec. 5, 1991).

Representative examples of suitable linear SiH-containing compounds include 1,1,3,3-tetraalkyldisiloxane, dialkylhydrogensiloxy-endstopped polydialkylsiloxane, copolymer comprising at least two alkylhydrogensiloxy groups, (e.g., $(CH_3)_2(H)SiO[(CH_3)_2SiO]_x[(CH_3)(H)SiO]_y$-$Si(H)(CH_3)_2$, where x and y are greater than or equal to 1). Other examples of SiH-containing compounds useful in the invention include 1,1,3,3-tetramethyldisiloxane, 2,4,6,8-tetramethylcyclotetrasiloxane, methyldimethoxysilane, triethylsilane, and methyldiethoxysilane. Other examples include compounds of the formulae:

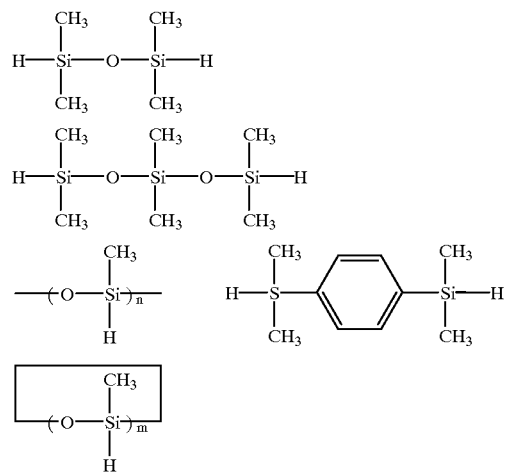

where m and n are integers and n is from about 4 to about 5000 and m is from about 3 to about 20.

The preferred linear SiH-containing silicon compound for Component (B) in the present invention is 1,1,3,3-tetramethyldisiloxane. The preferable cyclic hydride polysiloxane is 2,4,6,8-tetramethylcyclotetrasiloxane.

The preferred Component (B) in the present invention is the aforementioned 1,1,3,3-tetramethyldisiloxane.

Component (B) is used in the method and composition of the present invention in an amount ranging from about 0.5 to about 400, preferably from about 0.5 to about 100, and most preferably from about 0.75 to about 5, parts by weight as compared to the weight of Component (A).

Component (C) of the present invention comprises a quaternary bis(onium) hexahaloplatinate hydrosilation catalyst of the formula $(R_4M)_2PtX_6$ wherein M is arsenic, phosphorous or nitrogen, X is Cl⁻ or Br⁻ preferably chlorine, and R is an organic radical comprising $C_{1-30}$, substituted or unsubstituted, linear alkyl, or an aryl, alkaryl or aralkyl radical. The R substituents may be the same or different in any given complex and may be, for example, methyl, ethyl, n-butyl, hexyl, stearyl, phenyl, tolyl, and benzyl. By the term "substituted" it is meant an organic radical having chloro, bromo, iodo, cyano, carboxy, mercapto, hydroxy, thio, amino, nitro, phospho or other functional groups as known in the art. Moreover, heterocyclic and aromatic heterocyclic organic radicals such as pyridyl, thiophenyl, pyranyl, and the like as known in the art are also meant to be encompassed in the definition of "substituted" organic radicals. The R substituents may also represent $R_3^1SiQ$— groups in which Q represents a divalent aliphatic hydrocarbon radical having from 1 to 6, inclusive, carbon atoms, for example, —$CH_2$—, —$CH_2CH_2$—, and —$CH_2CHCH_3CH_2$— and each $R^1$ represents an alkyl, aryl, aralkyl, or alkaryl radical as defined and exemplified for R, above, or one $R^1$ substituent may represent a trimethylsilyl radical.

The following examples are meant to be illustrative of suitable quaternary bis(onium) platinate hydrosilation catalysts useful in the practice of the invention:

$[(CH_3)_4N]_2PtCl_6$; $[(C_2H_5)_4N]_2PtCl_6$; $[(C_3H_7)_4N]_2PtCl_6$; $[(C_4H_9)_4N]_2PtCl_6$; $[(n-C_5H_{11})_4N]_2PtCl_6$; $[(n-C_6H_{13})_4N]_2PtCl_6$; $[(n-C_7H_{15})_4N]_2PtCl_6$; $[(n-C_8H_{17})_4N]_2PtCl_6$; $[(n-C_{18}H_{37})_4N]_2PtCl_6$; $[(n-C_4H_9)_4P]_2PtCl_6$; $[(C_6H_5)_4P]_2PtCl_6$; $[(C_6H_5)_4As]_2PtCl_6$; $[(C_4H_9)_4N]_2PtBr_6$; $[(C_4H_9)_4P]_2PtBr_6$; $[poly-CH_2N^+(C_4H_9)_3]_2PtCl_6^{-2}$; and $[poly-CH_2P^+(C_4H_9)_3]_2 PtCl_6^{-2}$.

The preferred hydrosilation catalyst in the practice of the invention is $[(n-C_8H_{17})_4N]_2 PtCl_6$.

In the method of the invention the present catalysts are most useful and economical in the range of from about 1 to about 5000 parts per million, preferably from about 1 to about 500, and most preferably from about 10 to about 50 parts per million by weight, based upon the weight of Component (A).

Component (C) may be either first prepared, for example by the method set forth in the Iovel, et al. reference mentioned above, prior to addition to Component (A), (B), or both, or may be prepared by the in situ addition of a quaternary onium halide, sulfate, or other salt and a salt of hexahaloplatinic acid (e.g., potassium hexachloroplatinate) in the hydrosilation reaction mixture. As the hexahaloplatinate used to generate the catalysts of the invention can itself promote the epoxide ring-opening and hydrosilation addition reactions in the presence of silicon hydrides, it is preferred in the practice of the invention that the catalyst be pre-made prior to addition to a batch containing both Components (A) and (B). Otherwise there exists the possibility that some ring-opening polymerization might occur during the early stages of the hydrosilation reaction, with the concomitant adverse effects on viscosity control. The catalysts as described herein have been found to be effective for the selective hydrosilation reaction in the method of the invention, without also promoting an oxirane ring-opening polymerization reaction.

To practice the method and make the curable composition of the present invention, Components (A), (B) and (C) are brought together in a reaction vessel of suitable size for the size of the batch. Addition of the Components is preferably with mixing. A volatile solvent, preferably toluene, xylene or hexane, may also be added to the reaction mixture in order to facilitate the mixing process and dispersion of the Components.

The curable epoxysilicone composition of the invention is then prepared by reacting the mixture of Components (A), (B) and (C) at a temperature in the range of from about 25° C. to about 120° C., preferably from about 25° C. to about 110° C. and most preferably from about 50° C. to about 100° C. The temperature of the reaction mixture is then maintained until the completion of the addition reaction, which can be conveniently determined through IR spectroscopy by the disappearance of the strong absorbance at 2200 cm$^{-1}$ due to the SiH group.

A preferred curable composition of the present invention comprises a (cyclohexene oxide)ethyl silane or a (cyclohexene oxide)ethyl siloxane.

In one embodiment of the invention, the present composition is readily prepared by first mixing Components (A) and (B), either in a reaction vessel or otherwise. To initiate the hydrosilation reaction, Component (C) is thereafter added, preferably with mixing, and the temperature then held as described above.

In another embodiment of the invention, the present composition is prepared by mixing Component (A) or (B), or both, in a suitable reaction vessel, followed by the addition of the appropriate amount of quaternary onium salt used for producing Compound (C) of the method of the invention, and thereafter adding a salt of hexahaloplatinic acid in the amount as required for catalytic activity.

In another embodiment of the invention, any two of Components (A), (B) or (C), as defined above, can be pre-mixed, and the third Component then added later to produce the composition of the invention by the present method.

In yet another embodiment of the invention, any two of Component (A), Component (B), quaternary onium salt or hexahaloplatinate useful for producing Component (C) may be first mixed together. The additional components may then be added thereafter, either as a mixture or individually, and the reaction process of the invention then completed. Such mixtures in this and the previous embodiment exemplify that the Components of the invention may be pre-mixed so as to provide what is in practicing the invention essentially a two-component system for making a curable epoxysilicone.

After the completion of the hydrosilation reaction any volatile solvent previously added can be removed from the composition of the invention through evaporation, preferably at elevated temperature and reduced pressure.

The temperature of devolatilization may be between from about 50° C. to about 130° C., preferably between from about 50° C. and about 100° C. and most preferably between from about 80° C. to about 100° C. If a tertiary amine stabilizer is incorporated into the practice of the present invention, then the temperature of devolitization may be between from about 100° C. to about 250° C., preferably between about 125° C. and about 225° C., and most preferably between from about 150° C. and 200° C.

The pressure of the stripping step is generally preferred to be below atmospheric, as such reduced pressure aids in the release of volatile molecules from the composition of the invention. Preferably the stripping step is at less than 25 torr and most preferably at less than 10 torr.

The stripping of volatile molecules, including unreacted volatile Components and low molecular weight side products of the hydrosilation reaction, may be conveniently achieved through use of a rotary evaporator, thin film evaporator, wiped film evaporator or the like.

The curable composition of the invention can be applied to cellulosic and other substrates including paper, metal, foil, polyethylene-coated Kraft paper (PEK), supercalendered Kraft paper, polyethylene films, polypropylene films and polyester films. In general, coatings can be applied to these substrates at the desired thickness. For example, the composition of the invention is readily applicable by doctor blade. For applications as a release coating, the composition of the invention is applied at a thickness of between about 0.1 mil and about 10 mils; it is also convenient to refer to such coatings in terms of coat weights, typically about 1 g/m$^2$.

The application and dispersion of the curable composition of the invention to a substrate may be facilitated if the composition is added as a solution or dispersion in a volatile liquid carrier in which the epoxysilicone composition is soluble. When the curable composition is a polydimethylsiloxane, preferable volatile liquid carriers include, for example, hexane, xylene or toluene. It should be recognized, however, that when the curable composition of the invention is a copolymer, terpolymer, etc., the volatile solvent must be chosen such that the polymer is soluble in the solvent, which may depend upon the particular physical and chemical properties of the polymer as recognized in the art. The amount of volatile liquid carrier incorporated into the composition should not exceed about 3% by weight as compared to the total weight of the curable composition, if the advantages of using a relatively solvent-free composition are desired.

Curing of the composition of the invention can be either thermally or, in the presence of the appropriate photocatalyst and possibly cure accelerator, through UV irradiation. It has been found that the presence of the quaternary bis(onium) haloplatinate of the composition of the invention does not substantially interfere with either of these curing methods.

Polymerization by heat involves the simple step of heating the epoxysilicones to a temperature of about 120° C. or greater, which causes the oxirane ring to open and thereby react. Reference is made in this regard to Pleudemann and Fanger, "Epoxyorganosiloxanes", *Journal of the American Chemical Society*, Vol. 81, pp. 2632–2635, 1959.

Polymerization by UV radiation involves the use of a photocatalyst that, when irradiated with UV light, forms an acid that catalyzes the crosslinking of epoxysilicone monomers through the epoxide ring-opening reaction. Such reactions are disclosed, for example, in U.S. Pat. No. 4,279,717 (Eckberg) and U.S. Pat. No. 4,617,238. Preparation of photoinitator salts useful for epoxysilicone polymerization are disclosed, for example, in Crivello and Lee, "Alkoxy-Substituted Diaryliodonium Salt Cationic Photoinitiators", *Journal of Polymer Science*, Part A: Polymer Chemistry, Vol. 27, John Wiley, New York 1989, pp. 3951–3968.

Cure performance of the composition of the invention and adhesion of the epoxysilicone product may be enhanced by the addition of epoxide monomers to the composition of the invention after the hydrosilation reaction is completed. For example, addition of up to 10 parts of an aliphatic epoxide monomer for every 10 parts epoxysilicone may result in composition exhibiting superior UV cured and anchorage on porous cellulose paper as compared to similar compositions without these "reactive diluents".

In order that persons skilled in the art may better understand the practice of the present invention, the following examples are provided by way of illustration, and not by way of limitation. Additional information which may be useful in state-of-the-art practice may be found in each of the references and patents cited herein, which are hereby incorporated by reference.

EXPERIMENTAL

Unless otherwise indicated, all resins and catalysts are available from General Electric Silicones, Waterford, N.Y. 1,1,3,3-tetramethyldisiloxane and n-butyl silane were purchased from Silar Laboratories. Quaternary onium salts used to generate the catalysts of the invention are commercially available from the Aldrich Chemical Co. $^1$H NMR spectra were recorded on a Varian XL 200-MHz spectrometer, a Hewlett-Packard 5840A Gas Chromatograph was used for gas phase chromatographic analysis.

While in practicing the invention a quaternary ammonium haloplatinate salt can be used directly as a selective hydrosilation catalyst, in most of the Examples described below a 1:2 mixture of the quaternary ammonium haloplatinate salt with an quaternary ammonium halide (usually tetra-n-butylammonium bromide) was used to increase the stability of the catalytic system towards colloid formation and to prevent oxirane ring-opening polymerization.

In the shorthand notation of epoxysilicone structure below, the following applies:

$M^e$ represents

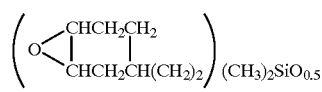

EXAMPLE 1
Ring-Opening Polymerization of Cyclohexene Oxide

To 2.0 g of cyclohexene oxide there were added 4 drops (about 0.2 mL) of the Ashby catalyst, and the mixture stirred at room temperature. Next, 40 μL n-butyl silane was introduced, with mixing, into the cyclohexene oxide/catalyst mixture. A very rapid, exothermic epoxide ring-opening polymerization occurred resulting in the production of poly (cyclohexene oxide).

Comparative Example 1A

There were dissolved in 2.0 g cyclohexene oxide, 10.0 mg tetra-n-butylammonium bromide. To this mixture were added with stirring 0.2 mL Ashby catalyst and 40 μL n-butylsilane. No heat release, color change, or viscosity change were noted. No polymeric products were formed based on gel permeation chromatography analysis.

EXAMPLE 2

Combined together at room temperature were 2.0 g cyclohexene oxide, 2.0 g 1,1,3,3-tetramethyldisiloxane, and 5 mg chloroplatinic acid. A very rapid, exothermic epoxide polymerization ensued after a brief induction period.

Comparative Example 2A

The reaction of Example 2 was repeated replacing chloroplatinic acid with [(n-C$_4$H$_9$)$_4$N]$_2$PtCl$_6$. No polymerization was noted even after standing 24 hours at room temperature.

EXAMPLE 3
Preparation of Epoxy-Silicone Monomers and Polymers

Into a 100 mL round bottom flask equipped with a magnetic stirrer and a reflux condenser were added 4.0 g 4-vinylcyclohexene oxide, 2.0 g poly(methylhydrogen siloxane), M$_n$=4700 g/mol, and 30 mL dry toluene. To this were added 5 mg of a 1:2 mixture of [(n-C$_4$H$_9$)$_4$N$^+$]$_2$PtCl$_6^-$ 2/(n-C$_4$H$_9$)$_4$N$^+$Br$^-$ and the resulting solution heated to 115–120° C. in an oil bath. After 24 hours, the poly(methyl- 2-ethyl[4-cyclohexyl(1,2)epoxy] siloxane) product was isolated in quantitative yield by removing the solvent under vacuum. No gel formation indicative of ring-opening polymerization was observed. The structure of the polymer was confirmed by $^1$H-NMR spectroscopy to be

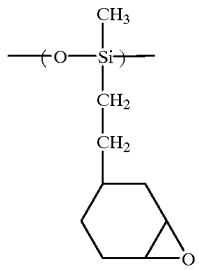

EXAMPLE 4

Following procedure of Example 3, 4.0 g 4-vinylcyclohexene oxide, 4.0 g of a 50:50 poly(dimethylsiloxane)-poly(methylhydrogensiloxane) copolymer, 30 mL toluene and 5 mg of a 1:2 mixture of $[(n-C_4H_9)_4N^+]_2PtCl_6^{-2}/(n-C_4H_9)_4N^+Br^-$ were combined in a 100 mL round bottom flask and heated to 115–120° C. for 24 hr. Obtained in a quantitative yield was a polymer of the structure

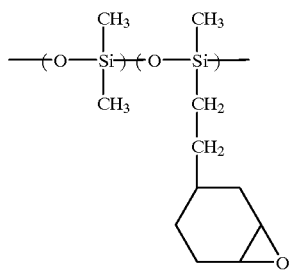

No evidence of ring-opening polymerization was observed.

EXAMPLE 5

Mixed together were 4.0 g 4-vinylcyclohexene oxide, 2.0 g 2,4,6,8-tetramethylcyclotetrasiloxane, 30 mL toluene, and 5 mg of a 1:2 mixture of $[(n-C_4H_9)_4N^+]_2PtCl_6^{-2}/(n-C_4H_9)_4$ $N^+Br^-$. This reaction mixture was heated for 20 hours at a temperature of 115 to 120° C. to give the desired cyclic tetrafunctional silicone epoxide shown below. The product was isolated after removing the solvent and excess starting materials under vacuum as described above.

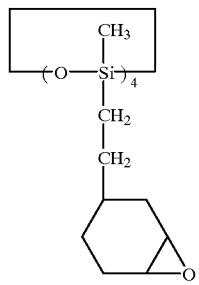

Again, no evidence of ring-opening polymerization was observed.

EXAMPLE 6

The reaction of Example 5 was repeated replacing the cyclic silane with 2,2,4,4,6,6-hexamethylcyclotetrasiloxane. On workup, as described above, there was obtained a quantitative yield of a product whose structure is given below based on the method of preparation.

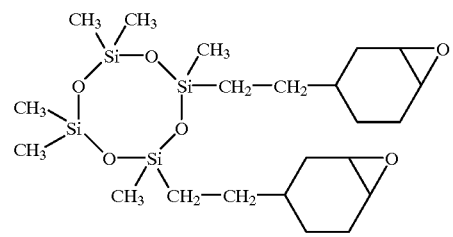

Only the monomer indicated above was isolated. There was no evidence of epoxide ring-opening polymerization which would have given a gelled product.

EXAMPLE 7

A difunctional silicone epoxide was prepared by the addition of 4.0 g 4-vinylcyclohexene oxide, 3.35 g 1,1,3,3,5,5-hexamethyltrisiloxane, 30 mL toluene, and 5 mg of a 1:2 mixture of $[(n-C_4H_9)_4N^+]_2PtCl_6^{-2}/(n-C_4H_9)_4N^+Br^-$. After 26 hours at 115 to 120° C. there was isolated the desired monomer shown below as the only product of the reaction.

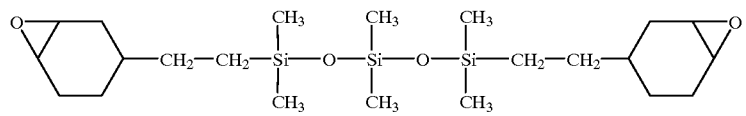

EXAMPLE 8

The reaction of Example 7 was repeated in all details with the exception that 1,1,3,3,5,5,7,7-octamethyltetrasiloxane was used. After workup, including evaporation under vacuum of the solvent and any remaining volatile starting materials, there were obtained a quantitative yield of the monomer indicated below.

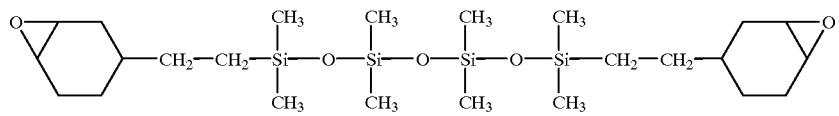

EXAMPLES 9–16

The Preparation of Epoxysilicone Monomers in the Absence of Solvents

The following reactions were carried out using different quaternary ammonium and phosphonium hexahaloplatinate salts as catalyst.

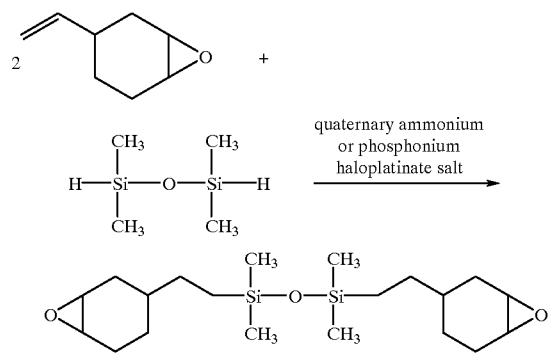

There were combined in a 100 mL round bottom flask equipped with a magnetic stirrer and reflux condenser 4.0 g 4-vinylcyclohexene oxide, 2.0 g 1,1,3,3-tetramethyldisiloxane with 5 mg of a 1:2 mixture of the haloplatinate salt and either a tetraalkylammonium or tetraalkyl phosphonium halide. The mixtures were heated at 80–85° C. in an oil bath and then examined for the presence of ring-opening polymerization after 6–18 hr. In all cases in which quaternary ammonium and phosphonium haloplatinate salts were used, only hydrosilation was noted with consequent formation of the desired difunctional epoxide and no indication of ring-opening polymerization was observed.

Comparative Examples 9A, 9B and 9C

In contrast to the results obtained in the reactions of Examples 9–16, when conventional Ashby, Lamoreaux or Karstedt catalysts were employed under the otherwise same reaction conditions, very rapid gelation due to the oxirane ring-opening reaction was observed.

In Table 1, the stability and reactivity of the quaternary ammonium, phosphonium and arsonium hexahaloplatinate salts used to catalyze the various hydrosilation addition reactions in Examples 9–16 and Comparative Examples 9A, 9B and 9C are summarized.

TABLE 1

Stability and Reactivity of Various Quaternary Ammonium and Quaternary Phosphonium Haloplatinate Salts

| EXAMPLE | CATALYST | REACTION TIME |
| --- | --- | --- |
| 9 | $[(C_8H_{17})_4N]_2PtCl_6/(C_8H_{17})_4NBr$ | 9 hr |
| 10 | $[(C_7H_{15})_4N]_2PtCl_6/(C_7H_{15})_4NBr$ | 9 hr |
| 11 | $[(n-C_4H_9)_4P]_2PtCl_6/(n-C_4H_9)_4PBr$ | 12 hr |
| 12 | $[(n-C_4H_9)_4N]_2PtCl_6/(n-C_4H_9)_4NBr$ | 12 hr |
| 13 | $[(C_6H_5)_4P]_2PtCl_6/(C_6H_5)_4PBr$ | 6 hr |
| 14 | $[(C_6H_5)_4As]_2PtCl_6/(C_6H_5)_4AsCl$ | 6 hr |
| 15 | $[poly-CH_2-N(n-C_4H_9)_3]_2PtCl_6/$ $[poly-CH_2-N(n-C_4H_9)_3]Br$ | 18 hr |
| 16 | $[poly-CH_2-P(n-C_4H_9)_3]_2PtCl_6/$ $[poly-CH_2-P(n-C_4H_9)_3]Br$ | 18 hr |
| 9A | Ashby Catalyst | Rapid Gelation |
| 9B | Lamoreaux Catalyst | Rapid Gelation |
| 9C | Karstedt Catalyst | Rapid Gelation |

As a further aid to those practicing the invention, Table 2 sets forth the melting point or decomposition temperature of selected catalysts which have been made and found useful in the method and curable composition of the invention.

TABLE 2

| COMPOUND | MELTING POINT (° C.) | DECOMPOSITION (° C.) |
| --- | --- | --- |
| $[R_4N]_2PtCl_6$ | | |
| R = $CH_3$ | | >250 |
| $C_2H_5$ | | >230 |
| $C_3H_7$ | | >210 |
| $C_4H_9$ | 202–205 | |
| $n-C_5H_{11}$ | 102–104 | |
| $n-C_6H_{13}$ | | >194 |
| $n-C_7H_{15}$ | | >210 |
| $n-C_8H_{17}$ | | >195 |
| $n-C_{18}H_{37}$ | 107–109 | |
| $[R_4P]_2PtCl_6$ | | |
| R = $n-C_4H_9$ | 108–110 | |
| $C_6H_5$ | >230 | |
| $[(C_6H_5)_4As]_2PtCl_6$ | | >220 |
| $[(C_4H_9)_4N]_2PtBr_6$ | | >190 |
| $[(C_4H_9)_4P]_2PtBr_6$ | | >130 |

It is understood that various other modifications will be apparent to and can be readily made by those skilled in the art without departing from the scope and spirit of the present invention. Accordingly, it is not intended that the scope of the claims appended hereto be limited to the description set forth above but rather that the claims be construed as encompassing all of the features of patentable novelty which reside in the present invention, including all features which would be treated as equivalents thereof by those skilled in the art to which the invention pertains.

What is claimed is:

1. A method of preventing colloid formation by a haloplatinate catalyst for the hydrosilation of an ethylenically unsaturated epoxide comprising the steps of:

(i) providing a hydrosilation reaction mixture comprising an ethylenically unsaturated epoxide and an organohydrogen siloxane or an organohydrogensilane;

(ii) mixing in the mixture of step (i) a quaternary ammonium, phosphonium, or arsonium salt, said salt containing a cationic species of the formula $MR_4^+$ where M is nitrogen, phosphorus, or arsenic and the R groups are, individually, organic radicals comprising $C_{1-30}$, substituted or unsubstituted, linear alkyl, or an aryl, alkaryl, or aralkyl radical and a salt of hexahaloplatinic acid; and (iii) reacting the quaternary ammonium, phosphonium, or arsonium salt with the salt of hexahaloplatinic acid to form in situ a haloplatinate hydrosilation catalyst in the hydrosilation mixture and wherein the haloplatinate hydrosilation catalyst promotes the hydrosilation reaction without promoting a ring opening polymerization of the epoxide.

2. The method of claim 1 wherein the quaternary ammonium, phosphonium, or arsonium salt is tetra-n-butyl ammonium bromide.

3. The method of claim 2 wherein the salt of hexahaloplatinic acid is potassium hexachloroplatinate.

4. The method of claim 1 wherein the salt of hexahaloplatinic acid is added after the quaternary ammonium, phosphonium, or arsonium salt has been added to the hydrosilation mixture.

5. The method of claim 4 wherein the salt of hexahaloplatinic acid is potassium hexachloroplatinate.

6. The method of claim 5 wherein the quaternary ammonium, phosphonium, or arsonium salt is a quaternary ammonium halide.

7. The method of claim 6 wherein the quaternary ammonium halide is tetra-n-butyl ammonium bromide.

* * * * *